United States Patent [19]

Peterson et al.

[11] 4,434,663
[45] Mar. 6, 1984

[54] ELECTROMAGNETIC ACOUSTIC TRANSDUCER

[75] Inventors: William E. Peterson, Thousand Oaks, Calif.; Robert B. Thompson, Ames, Iowa

[73] Assignee: Rockwell International Corporation, El Segundo, Calif.

[21] Appl. No.: 338,776

[22] Filed: Jan. 11, 1982

[51] Int. Cl.³ .......................................... G01N 29/04
[52] U.S. Cl. ...................................................... 73/643
[58] Field of Search .......................................... 73/643

[56] References Cited

U.S. PATENT DOCUMENTS

| | | |
|---|---|---|
| 3,850,028 | 11/1974 | Thompson et al. |
| 3,918,295 | 11/1975 | Herbertz ............................ 73/643 |
| 4,048,847 | 9/1977 | Alers et al. |
| 4,102,207 | 7/1978 | Frost et al. ........................... 73/643 |
| 4,104,922 | 8/1978 | Alers et al. |
| 4,127,035 | 11/1978 | Vasile . |
| 4,218,924 | 8/1980 | Fortunko et al. |
| 4,232,557 | 11/1980 | Vasile . |
| 4,295,214 | 10/1981 | Thompson . |
| 4,296,486 | 10/1981 | Vasile . |

*Primary Examiner*—Anthony V. Ciarlante
*Attorney, Agent, or Firm*—H. Fredrick Hamann; Craig O. Malin; John J. Deinken

[57] ABSTRACT

Disclosed is an electromagnetic acoustic transducer for use with electrically conductive objects. The transducer includes an electromagnet for establishing a static magnetic field directed into the object in a first region and directed out of the object in a second region. A meander coil for inducing eddy currents in the object when an alternating current is applied to the coil includes a first serpentine printed circuit on a first side of a printed circuit board and a second serpentine printed circuit on a second side of the board. The source and the coil are so oriented that the vector product of the field and the eddy currents produces an instantaneous force field in the object which is periodically alternately oriented.

14 Claims, 4 Drawing Figures

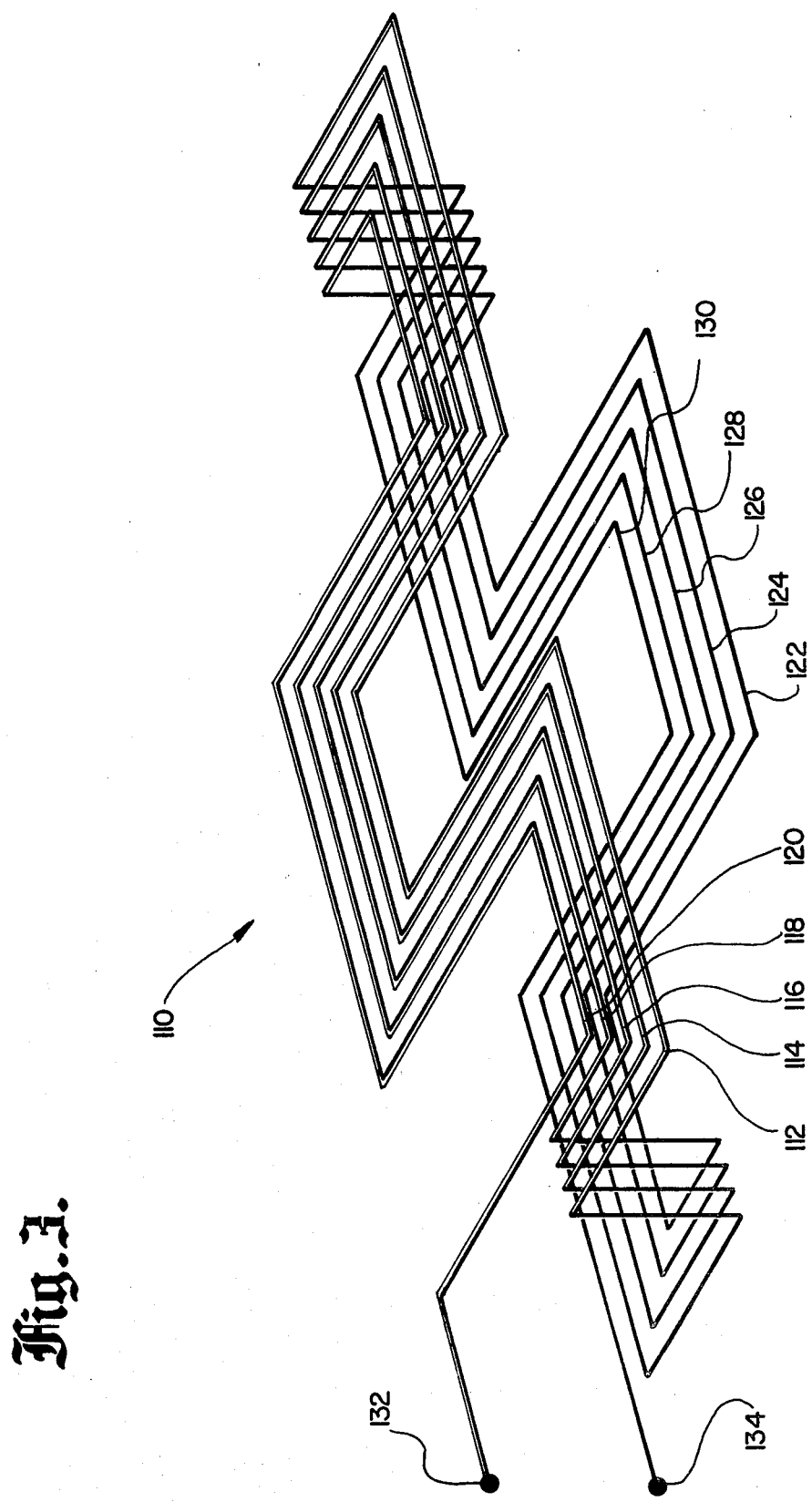

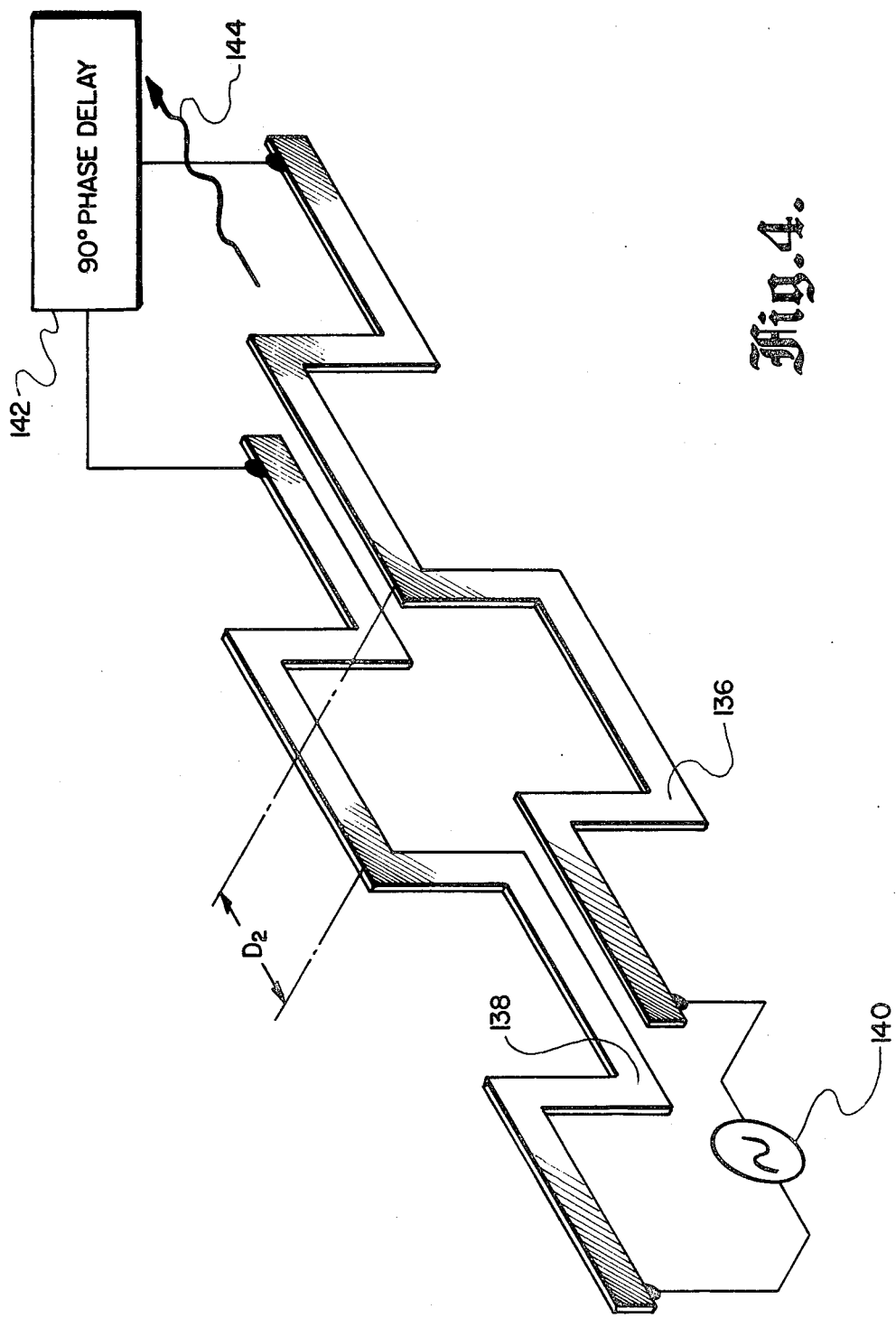

ELECTROMAGNETIC ACOUSTIC TRANSDUCER

GOVERNMENT RIGHTS

The Government has rights in this invention pursuant to Contract No. DTFR53-80-C-00121, awarded by the Federal Railroad Administration.

BACKGROUND OF THE INVENTION

This invention relates to techniques for generating and detecting ultrasonic waves and, more particularly, to electromagnetic acoustic transducers.

Efficiency and economy have been increasingly emphasized in many areas of modern structural design, and this emphasis has stimulated the more widespread use of nondestructive testing techniques. Before nondestructive methods were developed, it was necessary to assume, in designing structural components, that flaws of a certain size were present in the construction materials. This design technique called for the selection of structural components which were sufficient in size and strength to function properly even when the assumed defects were present. Nondestructive testing methods, however, are capable of locating structural defects at an early stage in the life of a flaw, so that the appropriate corrective action, such as removing and replacing a defective component, can be accomplished before a defect causes a catastrophic failure. Consequently, where nondestructive testing can be implemented during their operational life, structural components may be manufactured and assembled more economically by reducing their dimensions and substituting lower strength, less expensive materials. Nondestructive inspection techniques can thus be utilized to maintain a desired level of reliability in a structure while concurrently reducing construction and materials costs.

One of the many types of nondestructive testing is ultrasonics, in which the interaction between acoustic wave energy and the internal structure of an object is analyzed to predict the physical integrity of the object. A key element in any ultrasonic nondestructive testing system is the transducer, which is used to convert electrical energy into acoustic wave energy in the test object and also to convert the acoustic energy back into electrical energy for detection purposes. Traditionally, the high conversion efficiency and modest cost of piezoelectric materials have led to their widespread use as ultrasonic transducers in many applications. Piezoelectric transducers are disadvantaged, however, by the need to be coupled to the ultrasonic medium through a liquid or solid bond.

Consequently, requirements for operation at high speeds, at elevated temperatures, in remote locations, with broadband and reproducible acoustic coupling, and without the subsequent cleanup of a liquid bond have spurred the development of noncontact ultrasonic techniques, such as electrostatic transducers, optical techniques, and electromagnetic transducers, which have supplanted piezoelectric transducers in many applications. One of the most promising noncontact transducers is the electromagnetic acoustic transducer (EMAT). An EMAT consists of a conductor which is positioned within a static magnetic field near the surface of a conducting material. When a radio frequency is applied to the conductor, eddy currents are induced in the material. If the magnetic field and the conductor are properly oriented, the Lorentz forces exerted on the eddy currents by the magnetic field will be transmitted to the lattice structure of the material and generate an ultrasonic wave. Reduced inspection time, an ability to operate in remote and inaccessible locations, and reduced transducer wear are some of the significant advantages offered by an EMAT-based nondestructive testing system.

EMATs have been fabricated with a variety of coil and magnet configurations to suit the requirements of particular applications. U.S. Pat. Nos. 3,850,028; 4,048,847; 4,080,836; 4,092,868; 4,104,922; 4,127,035; 4,184,374; 4,218,924; 4,232,557; and 4,248,092, for example, the teachings of which are incorporated herein by reference, illustrate some of the approaches which have been utilized. While EMATs have thus been employed to great advantage in many testing situations, some significant limitations of previous EMAT designs have been identified. The periodic permanent magnet EMAT, for example, which is best described in U.S. Pat. No. 4,127,035 and is illustrated herein in FIG. 1, is important because it can be used to generate certain types of ultrasonic waves, such as horizontally polarized shear (SH) waves, which are difficult or impossible to produce with other transducer designs. The fabrication of a periodic permanent magnet EMAT, however, requires extensive precision machine work to produce permanent magnets of the proper dimensions for the EMAT. In addition, the periodically varying magnetic field which is required is difficult to produce with electromagnets, although the use of electromagnets would be desirable in some applications because of the higher strength magnetic fields which could thereby be provided. Consequently, a need has developed for a new EMAT which will exhibit the advantages of the periodic permanent magnet EMAT while avoiding the limitations of that design.

SUMMARY OF THE INVENTION

It is a general objective of this invention to provide a new and improved electromagnetic acoustic transducer.

The transducer of this invention, which is designed to be used in conjunction with an electrically conductive object, includes a source of magnetic flux for establishing a static magnetic field in the object and a meander coil for inducing eddy currents in the object when an alternating current is applied to the coil. The coil includes a first serpentine element which is positioned within one magnetic field and a second serpentine element positioned adjacent to the first element. The source and the coil are oriented so that the vector product of the field and the eddy currents produces an instantaneous force field in the object which is periodically alternately oriented.

In a more particular embodiment, the first serpentine element includes a plurality of conductors and the second serpentine element includes another plurality of conductors. The first and second serpentine elements in this embodiment are connected so that current passing through the meander coil will alternately pass through conductors of the first and second serpentine elements.

In another more particular embodiment, the first and second serpentine elements are staggered by an amount equal to half of the periodicity and the transducer further includes a 90° phase delay circuit connected between the first and second serpentine elements, the transducer thereby being adapted to transmit in or receive from a single direction.

The magnetic flux required in these EMATs may be supplied by an electromagnetic having a single pole directed toward the object such that the static magnetic field is a unidirectional field. The magnetic flux may alternatively be supplied by an electromagnetic having a first and second poles directed toward the object such that the static magnetic field is directed into the object in a first region and out of the object in a second region. The meander coil may include a first serpentine printed circuit on a first side of a printed circuit board and a second serpentine printed circuit on a second side of the board.

A method of generating an acoustic wave in an electrically conductive object includes, according to this invention, the steps of providing a source of magnetic flux to establish a static magnetic field in the object; positioning a meander coil, including adjacent first and second serpentine elements, within the static magnetic field; applying an alternating current to the coil to induce eddy currents in the object; and orienting the source of magnetic flux and the coil so that the vector product of the field and the eddy currents produces an instantaneous force field in the object which is periodically alternately oriented.

A method of detecting an acoustic wave in an electrically conductive object includes, according to this invention, the steps of providing a source of magnetic flux to establish a static magnetic field in the object; positioning a meander coil, which includes adjacent first and second serpentine elements, within the static magnetic field; and orienting the source of magnetic flux and the coil so that the vector product of the field and eddy currents which is produced in the object by the acoustic wave generates an alternating current in the coil.

These examples summarize some of the more important features of this invention. There are, of course, additional details involved in the invention, which are further described below and which are included within the subject matter of the appended claims.

BRIEF DESCRIPTION OF THE DRAWINGS

Additional objectives, features, and advantages of the present invention will be evident from the description below of the preferred embodiments and the accompanying drawings wherein the same numerals are used to refer to like elements throughout all the figures. In the drawings:

FIG. 3 is a perspective view of an alternative meander coil for the EMAT shown in FIG. 2, and FIG. 4 illustrates another alternative coil design for the EMAT of FIG. 2.

DESCRIPTION OF THE PREFERRED EMBODIMENTS

Figure 1:
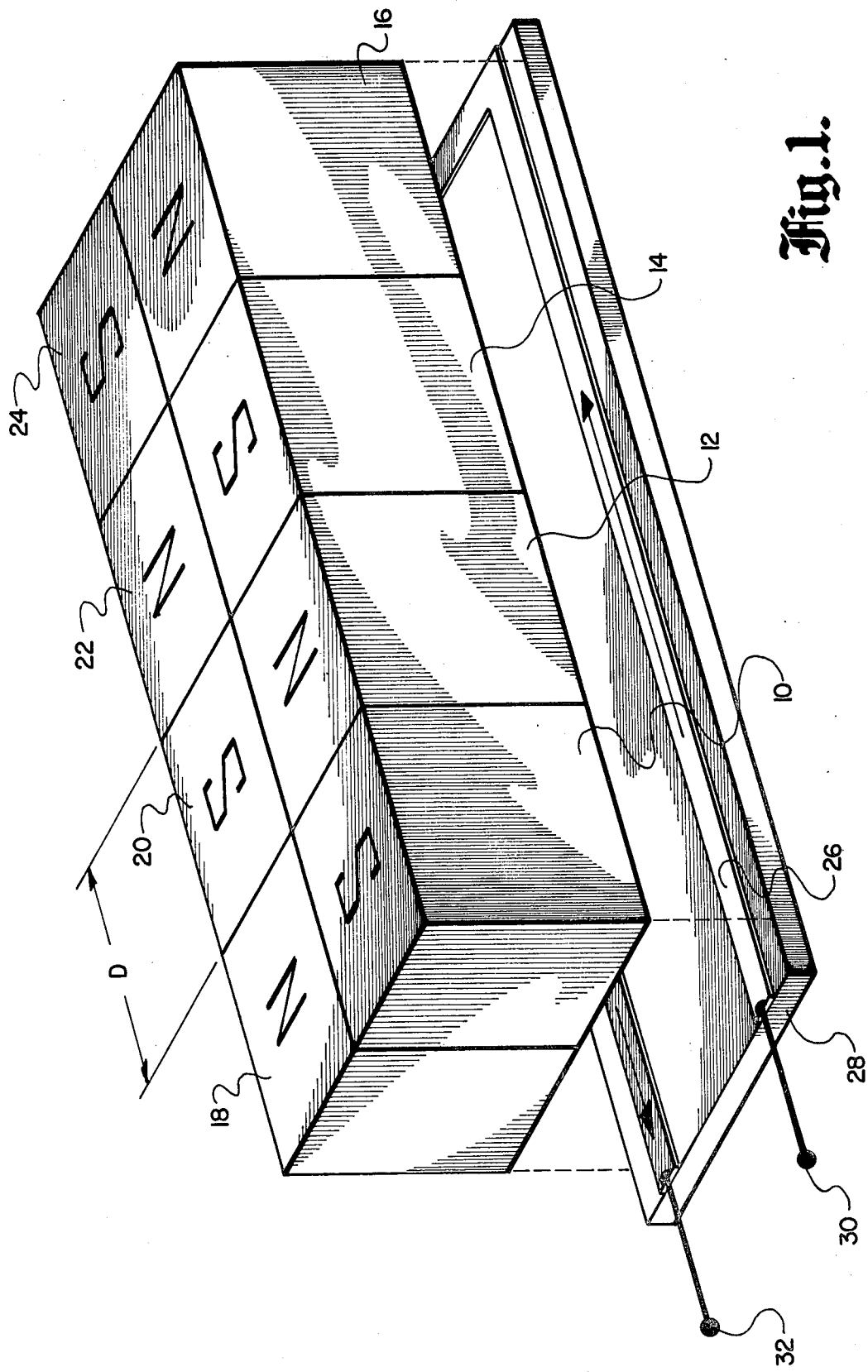
FIG. 1 illustrates in perspective view a periodic permanent magnet EMAT designed to generate horizontally polarized shear waves, an EMAT constructed according to the present invention is illustrated in a perspective view in FIG. 2.

FIG. 1 illustrates in perspective view a periodic permanent magnet (PPM) EMAT designed to generate horizontally polarized shear (SH) waves. This version of the PPM EMAT (other configurations are disclosed in U.S. Pat. No. 4,127,035) consists of a first row of permanent magnets 10, 12, 14, and 16, with a second row of magnets 18, 20, 22, and 24 placed adjacent to the first row. The magnets are oriented so that each magnet is reversed in polarity with respect to the magnets adjacent to it. A single turn coil 26 is placed in close proximity to the magnets (the EMAT is illustrated in an exploded view to more effectively depict the coil configuration). The coil 26 may be provided in the form of a wire or, as depicted in the drawing, a conductor which is deposited on a printed circuit board 28. When an alternating current is applied to the terminals 30 and 32 of the coil 26 while the EMAT is placed in close proximity to a conductive object, the eddy currents generated in the object by the coil current will interact with the periodic static field produced by the magnets to generate an SH wave in the object.

The magnets in the periodic permanent magnet EMAT must be precisely machined so that the length D of those magnets (the period of the EMAT) is equal to half the wavelength of the ultrasonic wave which is to be generated. This requirement effectively prevents the use of electromagnets in such an EMAT, since electromagnets for this application would require complex shaped pole pieces which would exhibit a large amount of flux leakage.

It is an outstanding feature of the present invention to provide a new EMAT which can be used in place of a periodic permanent magnet EMAT but does not exhibit the disadvantages of the latter design. One embodiment of this new EMAT is illustrated in a perspective view in FIG. 2. The EMAT includes an electromagnet 34 and a meander coil 36. The electromagnet includes pole pieces 38 and 40 which, when energized by a direct current applied to a magnet coil 42 by means of terminals 44 and 46, will establish a static magnetic field in an electrically conductive object 48 placed under the magnet, the field being represented by arrows 50, 52, 54, 56, 58, 60, 62, and 64. This field will be directed into the the object under one pole and out of the object under the other pole.

The meander coil 36 includes a first serpentine conductor 66 deposited on one side of a printed board 68 and a second serpentine conductor 70 deposited on the opposite side of the board. The first and second conductors are joined by a connection 72 through the board 68, so that when an alternating current is applied to terminals 74 and 76, the coil 36 will induce eddy currents in the object 48. The coil 36 is configured with a periodic pattern having a period D such that the pattern of the first serpentine conductor 66 is displaced from that of the second serpentine conductor 70 by 180°. With this arrangement, the relative directions of the instantaneous current in various portions of the coil 36 will be as indicated by the arrows 78, 80, 82, 84, 86, 89, 90, and 92. This current pattern will induce eddy current loops 94, 96, 98, and 100 in the object, which loops will alternate in current direction relative to adjacent loops. Thus, the vector product of the magnetic field, indicated by the arrows 50–64, and the eddy current loops 94–100 will produce an instantaneous force field in the object which is periodically alternately oriented, as represented by the arrows 102, 104, 106, and 108. The components of this force field will reverse direction with the frequency of the alternating current applied to the coil 36, thereby generating a horizontally polarized shear wave in the object 48. As will be appreciated by those skilled in the art, the EMAT shown in FIG. 2 may also be used to detect ultrasonic waves propogating in an object by a reciprocal process in which an alternating current is produced in the coil 36 by an ultrasonic wave travelling in the object.

By utilizing the coil construction of this invention, the periodic magnet structure and associated machining of the periodic magnet EMAT can be eliminated. The coil of this EMAT can readily be fabricated on a printed circuit board with precise dimensional control using the photolithographic techniques of solid state electronics technology. Moreover, a horseshoe type electromagnet may be employed to produce as large a static magnet field as desired. It is also possible to use a magnet with a single pole directed toward the object, such that the magnetic field covers only one side of the meander coil 36, for example.

Although the meander coil 36 has two periods, those skilled in the art will appreciate the meander coils with greater numbers of periods may be used to fit the requirements of particular applications. In addition, it may be desirable to add more meander coils connected in series (i.e., stacked under the magnet) to achieve additional current paths in the static magnetic field and thereby increase the intensity of the waves which are generated.

In some preliminary experiments to determine the characteristics of EMATs constructed according to this invention, the performance of such EMATs tuned to generate and detect 250 kHz SH waves was compared to that of periodic permanent magnet EMATs also tuned to 250 kHz. For each test, a pair of similar EMATs was placed 10 ¾" apart on a steel test sample, with one EMAT used to transmit the ultrasonic signal and the second arranged to receive the signal. When the same 250 kHz input RF signal was supplied to both types of EMAT, it was found that the pair of periodic permanent magnet EMATs produced an output signal measuring 68 millivolts peak-to-peak. The EMATs constructed according to this invention, however, generated an output of 88 millivolts peak-to-peak, thereby demonstrating an approximately 30% improvement in output amplitude over previous EMAT designs for generating and detecting horizontally polarized shear waves.

One of the problems with the use of EMATs in the past has involved the need to match the relatively low impedance of the EMAT coil to the higher impedance of the associated transmitting or receiving circuitry. This has been accomplished in some cases by the addition of an impedance matching circuit, but this solution can be undesirable because of the size of such matching circuits. Another solution to impedance matching for the EMAT of the present invention is illustrated in FIG. 3, which is a perspective view of an alternative meander coil 110 for the EMAT of FIG. 2. In this design, the first serpentine element of the coil includes a plurality of conductors 112, 114, 116, 118, and 120, and the second serpentine element includes a plurality of conductors 122, 124, 126, 128, and 130. These conductors are connected, as shown by the terminals 132 and 134, so that a current passing through the coil 110 will alternately pass through the conductors of the first and second serpentine elements. By providing an appropriate number of these conductors, whether by a wire winding technique or as printed conductors on a printed circuit board, the impedance of the coil 110 can be raised the necessary amount to match that of the associated transmitting or receiving circuitry.

Figure 2:
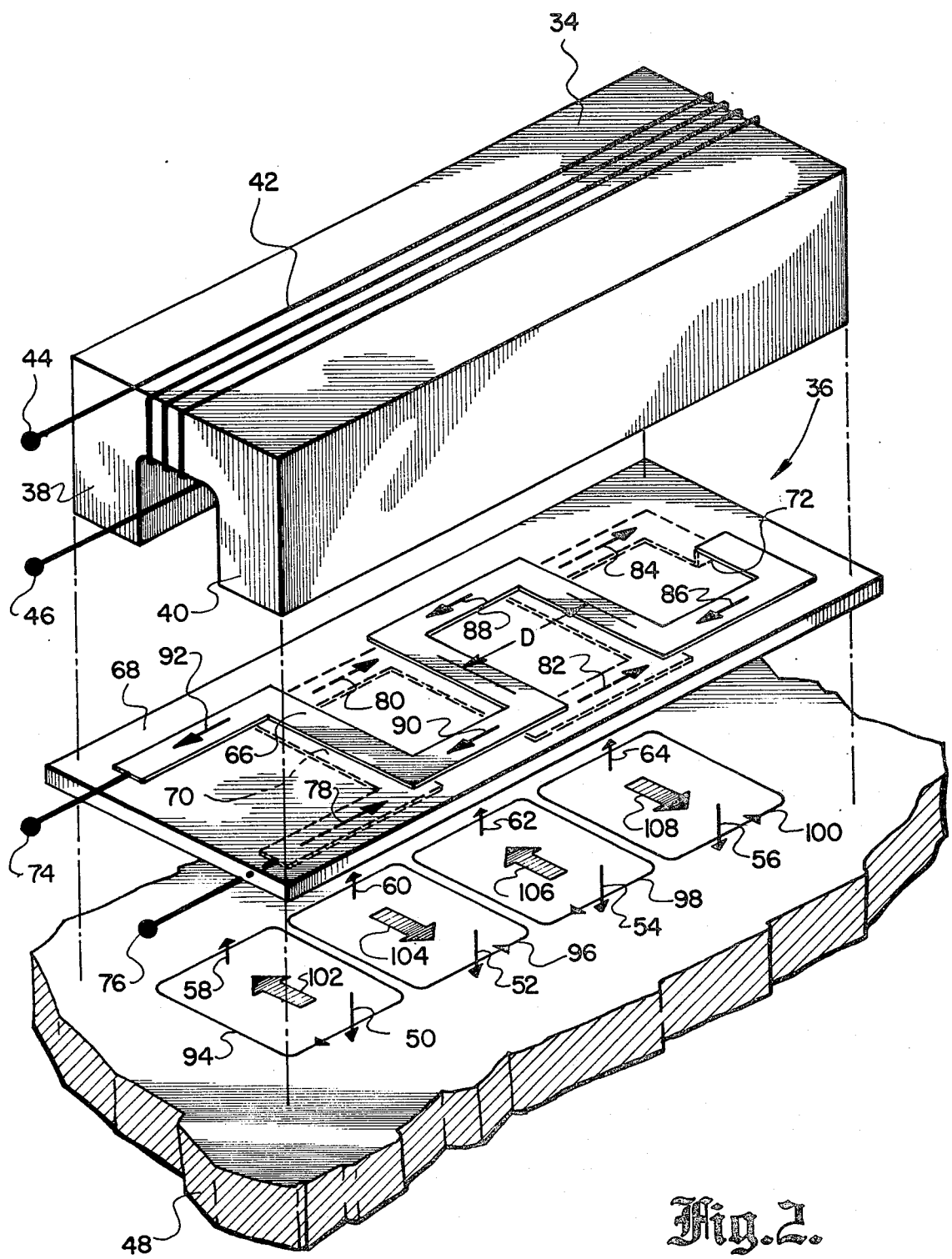

Another alternative coil design for the EMAT of FIG. 2 is shown in FIG. 4 in a plan, partially schematic view. Here, the first serpentine conductor 136 and the second serpentine conductor 138 are staggered so that their periodicity is offset by an amount equal to half that periodicity (D/2). In addition, the phase of an alternating current source 140 connected to the coil is delayed in the element 138 by 90° relative to the phase in the element 136 by connecting a 90° phase delay circuit 142 between the two elements. This arrangement causes the EMAT equipped with such a coil to generate an ultrasonic wave in a single direction, as represented schematically by the arrow 144. Such an EMAT will also selectively detect only that ultrasonic wave energy coming from a single direction.

Although some typical embodiments of the present invention have been illustrated and discussed above, modifications and additional embodiments of the invention will undoubtedly be apparent to those skilled in the art. Various changes, for example, may be made in the configurations, sizes, and arrangements of the components of the invention without departing from the scope of the invention. Furthermore, equivalent elements may be substituted for those illustrated and described herein, parts or connections might be reversed or otherwise interchanged, and certain features of the invention might be utilized independently of the use of other features. Consequently, the examples presented herein, which are provided to teach those skilled in the art how to construct the apparatus and perform the method of this invention, should be considered as illustrative only and not inclusive, the appended claims being more indicative of the full scope of the invention.

What is claimed is:

1. An electromagnetic acoustic transducer for use with an electrically conductive object, comprising:
   a source of magnetic flux for establishing a static magnetic field in the object and
   a meandor coil for inducing eddy currents in the object when an alternating current is applied to the coil, said coil including:
     a first serpentine element positioned within said magnetic field in a first plane perpendicular to said field and
     a second serpentine element positioned within said magnetic field adjacent to said first element and in a second plane parallel to said first plane,
     said elements being connected in series and so oriented that the current direction in said first element is opposite to the current direction in said second element at any instant,
   said source and said coil being so oriented that the vector product of said field and said eddy currents produces an instantaneous force field in the object which is periodically alternately oriented.

2. The transducer of claim 1, wherein
   said first serpentine element further comprises a first plurality of conductors; and
   said second serpentine element further comprises a second plurality of conductors.
   said first and second pluralities being connected in series, a first element conductor to a second element conductor.

3. The transducer of claim 1, wherein said first and second elements periodically vary in orientation with the same periodicity.

4. The transducer of claim 3, wherein said first and second serpentine elements are staggered by an amount equal to one fourth of said periodicity and further comprising a 90° phase delay circuit between said first and second serpentine elements, the transducer thereby being adapted to transmit in or receive from a single direction.

5. The transducer of claim 1, further comprising a printed circuit board, said first serpentine element comprising a first printed circuit on a first side of said board and said second serpentine element comprising a second printed circuit on a second side of said board.

6. The transducer of claim 5, wherein said source of magnetic flux further comprises an electromagnetic having a pole directed toward the object such that said static magnetic field is a unidirectional field.

7. The transducer of claim 5, wherein said source of magnetic flux further comprises an electromagnet having first and second poles directed toward the object such that said static magnetic field is directed into the object in a first region and out of the object in a second region.

8. The transducer of claim 6 or 7, wherein said electromagnet and said serpentine elements are oriented to generate a horizontally polarized shear wave.

9. An electromagnetic acoustic transducer for use with an electrically conductive object, comprising:
   an electromagnet for establishing a static magnetic field directed into the object in a first region and directed out of the object in a second region; and
   a meander coil for inducing eddy currents in the object when an alternating current is applied to the coil, said coil including:
      a first serpentine printed circuit on a first side of a printed circuit board, and
      a second serpentine printed circuit on a second side of said board,
   said circuits being connected in series and so oriented that the current direction in said first circuit is opposite to the current direction in said second circuit at any instant.
   said source and said coil being so oriented that the vector product of said field and said eddy currents produces an instantaneous force field in the object which is periodically alternately oriented.

10. An improved electromagnetic acoustic transducer for use with an electrically conductive object, of the type including a source of magnetic flux for establishing a static magnetic field in the object and an electrical conductor for inducing eddy currents in the object when an alternating current is applied to the conductor, wherein the improvement comprises a meander coil conductor including:
   a first serpentine element positioned within said magnetic field in a first plane perpendicular to said field and
   a second serpentine element positioned within said magnetic field adjacent to said first element and in a second plane parallel to said first plane,
   said elements being connected in series and so oriented that the current direction in said first element is opposite to the current direction in said second element at any instant.
   said source and said elements being so oriented that the vector product of said field and said eddy currents produces an instantaneous force field in the object which is periodically alternately oriented.

11. A method of generating an acoustic wave in an electrically conductive object, comprising the steps of:
   providing a source of magnetic flux to establish a static magnetic field in the object;
   positioning a meander coil, including adjacent first and second serpentine elements, within the static magnetic field such that the first element is in a first plane perpendicular to the field and the second element is in a second plane parallel to the first plane, the elements being connected in series and so oriented that the current direction in the first element is opposite to the current direction in the second element at any instant;
   applying an alternating current to the coil to induce eddy currents in the object; and
   orienting the source of magnetic flux and the coil so that the vector product of the feld and the eddy currents produces an instantaneous force field in the object which is periodically alternately oriented.

12. A method of generating an acoustic wave in an electrically conductive object, comprising the steps of:
   providing a source of magnetic flux to establish a static magnetic field in the object;
   positioning a meander coil, including adjacent first and second serpentine elements, within the static magnetic field such that the first element is in a first plane perpendicular to the field and the second element is in a second plane parallel to the first plane, the elements being connected in a series so oriented that the current direction in the first element is opposite to the current direction in the second element at any instant; and
   orienting the source of magnetic flux and the coil so that the vector product of the field and eddy currents produced in the object by the acoustic wave generates an alternating current in the coil.

13. The method of claim 11 or 12, wherein the step of providing a source of magnetic flux further comprises providing an electromagnetic having a pole directed toward the object such that the static magnetic field is a undirectional field.

14. The method of claim 11 or 12, wherein the step of providing a source of magnetic flux further comprises providing an electromagnet having first and second poles directed toward the object such that the static magnetic field is directed into the object in a first region and out of the object in a second region.

* * * * *